United States Patent [19]

Demarne et al.

[11] 4,235,897
[45] Nov. 25, 1980

[54] BENZODIAZEPINE DERIVATIVES AND PHARMACEUTICAL COMPOSITIONS THEREOF

[75] Inventors: Henri Demarne, Montpellier; André Hallot, St. Gely Du Fesc, both of France

[73] Assignee: C. M. Industries, Paris, France

[21] Appl. No.: 13,224

[22] Filed: Feb. 21, 1979

Related U.S. Application Data

[63] Continuation of Ser. No. 794,013, May 5, 1977, abandoned.

[30] Foreign Application Priority Data

May 5, 1976 [GB] United Kingdom ............... 18492/76

[51] Int. Cl.$^3$ .................... A61K 31/55; C07D 243/24
[52] U.S. Cl. ............................. 424/244; 260/239.3 D
[58] Field of Search ................. 260/239.3 D; 424/244

[56] References Cited

U.S. PATENT DOCUMENTS

| Re. 28,315 | 1/1975 | Schmitt | 260/239.3 D |
| 3,136,815 | 6/1964 | Reeder et al. | 260/239.3 D |
| 3,236,838 | 2/1966 | Archer et al. | 260/239.3 D |
| 3,516,988 | 6/1970 | Schmitt | 260/239.3 D |
| 3,718,646 | 2/1973 | Moffett | 260/239.3 D |
| 3,812,103 | 5/1974 | Metlesics et al. | 260/239.3D |

FOREIGN PATENT DOCUMENTS

1497456  9/1967  France .............................. 260/239.3 D

OTHER PUBLICATIONS

Sternbach et al. "Some Aspects of Structure-Activity Relationship in Psycotropic Agents of the 1,4-Benzodiazepine Series", *CSIR* New Delhi, India (1966).
Moffett et al. "J. Med. Chem.", vol. 15, No. 10, (1972), pp. 1079-1080.

*Primary Examiner*—John D. Randolph
*Assistant Examiner*—Robert T. Bond
*Attorney, Agent, or Firm*—Stevens, Davis, Miller & Mosher

[57] ABSTRACT

The invention relates to benzodiazepine compounds of the formula:

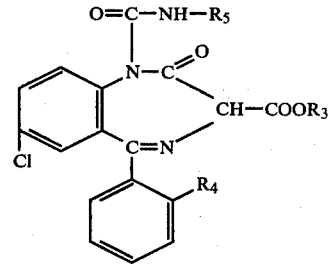

wherein $R_5$ is $C_1$–$C_4$ alkyl, $R_3$ is $C_1$–$C_4$ alkyl, and $R_4$ is selected from Cl and F, and medicaments containing such benzodizepine compounds.

5 Claims, No Drawings

BENZODIAZEPINE DERIVATIVES AND PHARMACEUTICAL COMPOSITIONS THEREOF

This is a continuation of application Ser. No. 794,013 filed May 5, 1977, now abandoned.

The present invention relates to new benzodiazepine derivatives, their preparation and their application in therapy.

The family of the benzodiazepines has been described over the course of many years, for example in French Pat. No. 1,497,456, and the action on the central nervous system of certain members of this family has also been described.

The continuation of the studies relating to the various products of the said family and also of related products has made it possible to show the interesting specific properties of certain sub-families of benzodiazepines. It is this which is the subject of the present invention.

The present invention concerns, as a sub-family of the benzodiazepines, the new products corresponding to the formula:

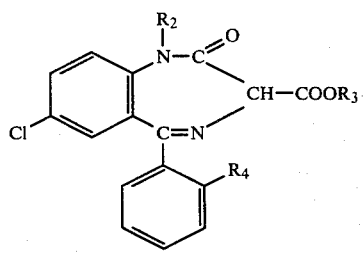

in which:

$R_2$ represents a radical chosen from amongst the allyl and propargyl radicals and the radical of the formula

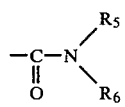

in which $R_5$ is chosen from amongst the hydrogen atom and a $C_1$-$C_4$-alkyl radical and $R_6$ is a $C_1$-$C_4$-alkyl radical, $R_3$ is a $C_1$-$C_4$-alkyl radical and $R_4$ is a halogen atom chosen from amongst bromime, chlorine and fluorine.

The compounds (I) are obtained by substitution of the nitrogen in the 1-position of the corresponding unsubstituted compounds of the formula (II):

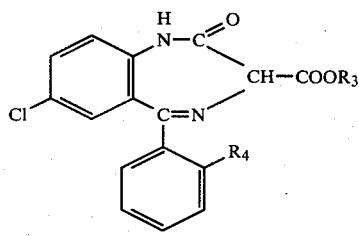

where $R_3$ and $R_4$ have the meanings indicated above.

The preparation of the compounds of the formula I is generally carried out by reacting a product of the formula II with a halide of the formula $X-R_2$. Hence the reaction of a product of the formula II with an allyl halide, a propargyl halide or a carbamoyl halide is used, the said halide being furthermore preferably a chloride, and this reaction being carried out in a dipolar aprotic solvent such as, for example, dimethylformamide or hexamethylphosphotriamide (HMPT) in the presence of sodium hydride. In the particular case where the radical

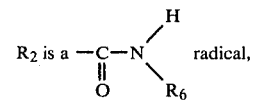

it is also possible to use, as the process of preparation, the reaction of a benzodiazepine of the formula II with an isocyanate of the formula $R_6N=C=O$; the reaction takes place in an inert solvent, such as benzene, in the presence of a catalyst such as para-toluenesulphonic acid.

The non-limiting examples which follow illustrate the invention.

EXAMPLE 1

7-Chloro-5-(2-chlorophenyl)-3-ethoxycarbonyl-1-methyl-carbamoyl-2-oxo-2,3-dihydro-1H-benzodiazepine

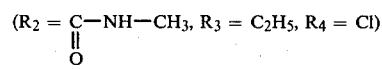

Code number CM 7,119.

2 grams of 7-chloro-3-ethoxycarbonyl-5-(2-chlorophenyl)-2-oxo-2,3-dihydro-1H-benzodiazepine-1,4 (the compound of the formula II in which $R_4$ is Cl and $R_3$ is $C_2H_5$) and 0.14 g of para-toluenesulphonic acid in 80 ml of anhydrous benzene are heated under reflux for 30 minutes, 8.4 ml of methyl isocyanate are then added and the mixture is heated under reflux for 7 hours.

After cooling, the benzene solution is stirred for 15 minutes with a 10% strength aqueous solution of sodium bicarbonate. Ether is added and the organic layer is separated off and dried over sodium sulphate. It is evaporated to dryness and the residue is taken up in hot cyclohexane and is allowed to crystallise. A colourless solid (1.2 g) is obtained. Melting point: 155°, with decomposition.

EXAMPLE 2

7-Chloro-5-(2-fluorophenyl)-3-ethoxycarbonyl-1-methylcarbamoyl-2-oxo-2,3-dihydro-1H-benzodiazepine ($R_2$=CO—NH—CH$_3$, $R_3$=C$_2$H$_5$, $R_4$=F) Code number CM 7, 120.

The procedure of Example 1 is followed, but replacing the benzodiazepine starting material by the product of the formula II in which $R_3$ is $C_2H_5$ and $R_4$ is F.

A colourless solid of melting point 169° C. (after recrystallisation from ether) is obtained.

EXAMPLE 3

7-Chloro-3-ethoxycarbonyl-5-(2-chlorophenyl)-1-propargyl-2-oxo-2,3-dihydro-benzodiazepine-1,4

($R_2$=CH$_2$—C≡CH, $R_3$=C$_2$H$_5$, $R_4$=Cl).

Code number CM 7,129.

3.8 g of a benzodiazepine of the formula II in which $R_3$ is $C_2H_5$ and $R_4$ is Cl are dissolved in 30 ml of hexamethylphosphotriamide under a nitrogen atmosphere, 1.2 g of sodium hydride (60% strength suspension in mineral oil) are then added over the course of 30 minutes and thereafter the mixture is stirred for 1 hour. 1.4 g of propargyl bromide are then added slowly and stirring is continued for 12 hours at ambient temperature.

The reaction mixture is poured into a saturated iced solution of ammonium chloride. The batch is extracted with methylene chloride and the organic phase is washed with water and then dried over sodium sulphate. After evaporating the solvent, the residue is taken up in ether and is allowed to crystallise. Colourless crystals are obtained. Melting point: 164° C.

EXAMPLES 4 AND 5

Following the procedure of Example 3, but varying the benzodiazepine starting material and/or the halide used, the products of the formula I listed in the table below were isolated.

| Code No. | $R_2$ | $R_3$ | $R_4$ | Melting point (solvent) |
|---|---|---|---|---|
| 7,128 | $CH_2CH=CH_2$ | $C_2H_5$ | Cl | 196° (ether) |
| 7,155 | $CH_2C\equiv CH$ | $C_2H_5$ | F | 173° (ethanol) |

The products according to the invention were subjected to pharmacological tests in order to determine their activity on the central nervous system. We shall indicate below the various tests to which the products were subjected.

In all cases the products were administered orally.

1. SPONTANEOUS ACTOGRAPHY

The animals are placed in individual cages through which pass two beams which strike two photoelectric cells.

During their movements, the animals (mice) intercept the beams and cause a recording on the impulse counters.

The variations in the motility of the treated animals are expressed in percentages relative to comparison animals; the sign (−) indicates a reduction (in percent) of the motility of the subjects.

2. TRACTION TEST

This consists of observing whether the animals (mice are capable of pulling themselves up on a horizontal bar gripped by the front paws.

This test demonstrates a sedative effect or a relaxing effect on the striped muscle.

The results are expressed as the 50% effective dose ($ED_{50}$), which is the dose (mg/kg) for which 50% of the mice can no longer pull themselves up.

3. ROTATING ROD TEST: EQUILIBRATION

Normal animals (mice) placed on a horizontal rod subjected to a rotational movement do not fall.

This test demonstrates the equilibration faculties of the normal animal, which disappear or are reduced in subjects which have been rendered ataractic.

The results are expressed as the 50% effective dose ($ED_{50}$) which is the dose (in mg/kg) for which 50% of the mice fall during the test.

ANTI-CONVULSIVE ACTIVITY IN RELATION TO PENTETRAZOL

When administered intraperitoneally at a dose of 125 mg/kg, pentylenetetrazol (or cardiazol) causes the appearance of lethal convulsions in 100% of the mice treated.

The active products administered orally prior to the cardiazol oppose the appearance of the convulsions and possibly allow the test animals to survive.

The results are expressed as the $ED_{50}$, that is to say as the dose (in mg/kg) which protects 50% of the animals.

ANTI-CONVULSIVE ACTIVITY IN RELATION TO ELECTRIC SHOCK

An alternating current of 12.5 volts is applied for 0.5 second by means of corneal electrodes to batches of 12 mice treated 1 hour beforehand with the product to be studied. The untreated mice subjected to this electric shock undergo a convulsion of the tonic type. For the treated mice, the number of mice which do not undergo a convulsion is noted and a percentage protection against convulsion is thus obtained.

The result is expressed as the 50% effective dose ($ED_{50}$) which is the dose (in mg/kg) for which 50% of the mice do not undergo a convulsion.

ANXIOLYTIC ACTIVITY: 4 PLATE TEST

The device is a parallelepiped chamber of which the floor consists of 4 metal plates of equal area. The experimenter can create a difference of potential which corresponds to a current of intensity 0.35 mA for a duration of 0.2 second, between each plate. Each time a mouse passes from one plate to the other, it receives an electric shock.

The anxiolytic agents cause an indifference to these electric shocks and as a result the treated mice cross from one plate to another more frequently than the comparison mice. 45 minutes after administration of the product to be studied the mice are placed in the chamber for 1 minute and the number of shocks received is measured and compared with the number of shocks received by the comparison animals. The results are expressed as a percentage increase in the number of shocks received by the treated animals relative to the comparison animals (which amounts to a percentage effect for a given dose), or as a threshold dose (TD) which is the lowest dose which produces a significant effect.

TOXICITY

Finally, for certain products, the $LD_o$ in mg/kg (for oral administration) has been provided.

The results obtained in these various tests are summarised in the table below. In this table are shown, by way of comparison products, the results obtained with related products which however do not belong to the family of the present invention; these comparison products are the following:

Number CM 7,243: a benzodiazepine in which $R_2$ is $CONHCH_3$, $R_4$ is Cl but the ethoxycarbonyl (or methoxycarbonyl) group in the 3-position is replaced by a hydrogen atom.

Number CM 7,264: a benzodiazepine in which $R_2$ in $CONHCH_3$, $R_4$ is F but the ethoxycarbonyl (or methoxycarbonyl) group in the 3-position is replaced by a hydrogen atom.

The products according to the invention can be used in human medicine for the treatment of neuropsychic disturbances such as anxiety, reactive depressive conditions and anxiety neuroses.

The active principle will be presented in appropriate forms for oral, parenteral or endorectal administration, for example drops, granules, cachets, pills, suppositories or injectable solutions.

The posology, which can vary in accordance with the afflications to be treated, can vary from 2 mg to 100 mg per day.

By way of example, these medicaments can be in the following forms:

| Pill: | | |
|---|---|---|
| | CM 7,119 | 2 mg |
| | tartaric acid | 6 mg |
| | talc | 107 mg |
| Tablet: | | |
| | CM 7,119 or 7,120 | 2 mg |
| | tartaric acid | 8 mg |
| | microcrystalline cellulose | 40 mg |
| | lactose | 68 mg |
| | Mg stearate | 2 mg |

TABLE

| | | Motor characteristics | | | Anti-convulsive action | | |
| | | Actography | | | | | |
| Product | Toxicity LD$_o$, mg/kg | dose mg/kg | % | Traction ED$_{50}$, mg/kg | Equilibration ED$_{50}$, mg/kg | Cardiazol ED$_{50}$, mg/kg | Electric shock ED$_{50}$, mg/kg | Anxiolysis 4 plates dose mg/kg |
|---|---|---|---|---|---|---|---|---|
| 7,119 | >300 | 0.5 | −40 | 20 | 48 | 0.75 | 20 | 1 |
| 7,120 | >300 | 2 | −45 | 8 | 64 | 0.50 | 20 | 1 |
| 7,128 | — | 100 | −77 | inactive | inactive | 10 | — | 8 |
| 7,129 | — | 2 | −64 | 10% to 6.25 | — | 10 | — | 5 |
| 7,155 | — | 15 | −68 | 10% to 25 | 200 | 5 | — | 8 |
| 7,243 | >300 | 0.125 | −66 | 2 | 2 | 0.2 | 32 | masked anxiolysis |
| 7,264 | >100 | 32 | −32 | 1 | 4 | 0.3 | 12 | TD>4 |

We claim:

1. A benzodiazepine compound of the formula:

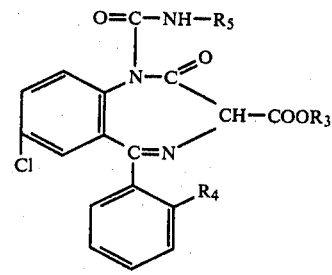

wherein:
R$_5$ is C$_1$—C$_4$ alkyl;
R$_3$ is C$_1$—C$_4$ alkyl; and
R$_4$ is selected from Cl and F.

2. A pharmaceutical composition useful for the treatment of neuropsychic disturbances, characterized in that it contains a compound as defined in claim 1 as active ingredient in association with a pharmaceutically acceptable carrier, and is administered in such a manner that the patient receives from 2 to 100 mg per day of the active ingredient.

3. A pharmaceutical composition useful for the treatment of anxiety, comprising an effective amount of a compound as defined in claim 1 in association with a pharmaceutically acceptable carrier.

4. A benzodiazepine compound as defined in claim 1, wherein
R$_5$ is methyl;
R$_3$ is ethyl; and
R$_4$ is chloro.

5. A benzodiazepine compound as defined in claim 1, wherein
R$_5$ is methyl;
R$_3$ is ethyl; and
R$_4$ is fluoro.

* * * * *